United States Patent [19]
Whitson et al.

[11] Patent Number: 5,968,096
[45] Date of Patent: Oct. 19, 1999

[54] METHOD OF REPAIRING PERFORATED SUBMUCOSAL TISSUE GRAFT CONSTRUCTS

[75] Inventors: Bryan Whitson, West Lafayette, Ind.; Boyle Cheng, Greeley, Colo.; Stephen F. Badylak, West Lafayette, Ind.

[73] Assignees: Purdue Research Foundation, West Lafayette; Clarian Health Partners, Indianapolis, both of Ind.

[21] Appl. No.: 08/908,151

[22] Filed: Aug. 6, 1997

Related U.S. Application Data

[62] Division of application No. 08/628,789, Apr. 5, 1996, Pat. No. 5,755,791.

[51] Int. Cl.⁶ .............................. A61F 2/02; A61F 2/10; A61K 35/38
[52] U.S. Cl. .............................. 623/15; 623/11; 424/422; 424/423; 424/424; 424/551
[58] Field of Search .................... 623/1, 11, 12, 623/16, 15; 424/422, 423, 424, 551

[56] References Cited

U.S. PATENT DOCUMENTS

| | | | |
|---|---|---|---|
| 2,127,903 | 8/1938 | Bowen | 128/334 |
| 3,562,820 | 2/1971 | Braun | 3/1 |
| 4,729,766 | 3/1988 | Bergentz | 623/1 |
| 4,902,508 | 2/1990 | Badylak et al. | 424/551 |
| 4,932,973 | 6/1990 | Gendler | 623/16 |
| 4,956,178 | 9/1990 | Badylak et al. | 424/551 |
| 5,002,572 | 3/1991 | Picha | 623/11 |
| 5,219,361 | 6/1993 | Von Recum | 623/11 |
| 5,275,826 | 1/1994 | Badylak et al. | 424/551 |
| 5,281,422 | 1/1994 | Badylak et al. | 424/551 |
| 5,306,304 | 4/1994 | Gendler | 623/16 |
| 5,350,583 | 9/1994 | Yoshizatu | 424/484 |
| 5,352,463 | 10/1994 | Badylak et al. | 424/551 |
| 5,372,821 | 12/1994 | Badylak et al. | 424/551 |
| 5,455,100 | 10/1995 | White | 428/131 |
| 5,496,372 | 3/1996 | Hamamoto et al. | 623/16 |
| 5,645,860 | 7/1997 | Knapp, Jr. et al. | 623/12 |
| 5,711,969 | 1/1998 | Patel et al. | 623/13 |

FOREIGN PATENT DOCUMENTS

WO 95/06439   3/1995   WIPO.

OTHER PUBLICATIONS

"Comparison of Bovine Collagen Xenografts to Autografts in the Rabbit", J.C. Tauro, et al., *Clinical Orthopaedics and Related Research*, No. 266, May, 1991, pp. 271–284.

"Development of a Reconstituted Collagen Tendon Prosthesis", Jack D. Goldstein, et al.,*The Journal of Bone and Joint Surgery*, Incorporated, vol. 71–A, No. 8, Sep. 1989, pp. 1183–1191.

"Replacement of Dog's Aorta by Autologous Intestinal Muscle in the Infected Retroperitoneum", R. Broll, et al., *Eurp. Surg. Res.*, 18: 390–396 (1986).

"Aortic Replacement with Multi–Layer Submucosa Prostheses Made From Heterologous Small Intestine", G. Rotthoff, et al., presented at 8th Congress of the International Society of Cardiovascular Surgery, Vienna, Sep. 7–9, 1967.

"Replacement of the Abdominal Aorta by an Ileum Muscle Tube in an Animal Experiment", J. Huth, et al., (translation), *Thoraxchir. Vask, Chir.*, 15(4): 401–407, Aug. 1967.

(List continued on next page.)

*Primary Examiner*—Mickey Yu
*Assistant Examiner*—Choon P. Koh
*Attorney, Agent, or Firm*—Barnes & Thornburg

[57] ABSTRACT

A perforated unitary multi-laminar tissue graft construct and method for preparing such construct is described. The method comprises overlapping strips of submucosa tissue with other strips of submucosal tissue, compressing at least the overlapped portions of said strips between two surfaces under conditions that allow or promote dehydration of the compressed submucosa sheets, and perforating the resulting unitary tissue graft construct. The perforated tissue graft compositions have enhanced mechanical and remodeling properties relative to non-perforated submucosal tissue grafts.

18 Claims, 1 Drawing Sheet

OTHER PUBLICATIONS

"Long Term Observations and Histological Studies on Vessel and Heart Wall Grafts From Small Intestine", R. Haring, et al., (translation), *Langenbecks Arch. Klin. Chir.*, 1965, 313:664–8.

"Replacement of the Abdominal Aorta With a Small–Intestine Muscle Tube In An Animal Experiment", J. Huth, (translation), *Zentralbl Chir.*, 92 (26/2): 1817–19 (1967).

"Reconstruction of the Arterial Flow Path by Autologous Intestinal Muscle Grafts in The Dog", H.P. Bruch, et al., (translation), *Folia Angiologica*, vol. 29 (3–5/81) pp. 65–68.

"Replacement of the Aorta by Multilayered Submucosa Prostheses of Heterologous Ileum", G. Rotthoff, et al., (translation), *Bulletin de la Societe International de Chirurgie*, No. 2, 1969, 256–259.

"The Effect of Lasar Drilled Holes on the Remodeling of a Novel Vascular Graft", Carr et al., (Abstract) Circulation, Oct. 1994, V. 90, N. 4, p. 143.

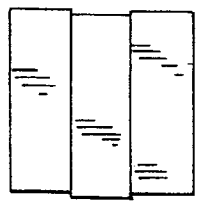 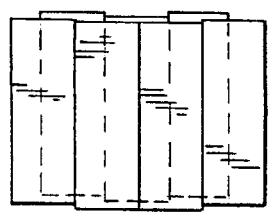 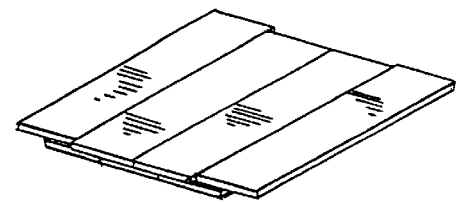
FIG. 1a　　　FIG. 1b　　　FIG. 1c
 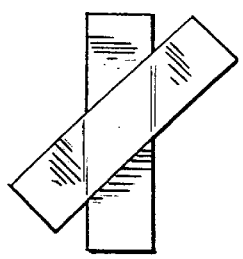 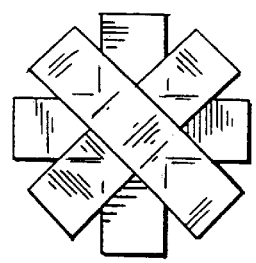
FIG. 2a　FIG. 2b　　　FIG. 2c
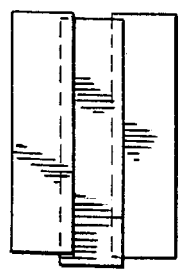 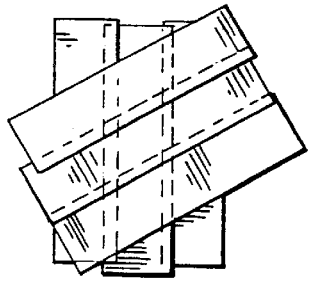 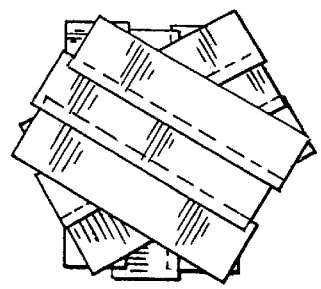
FIG. 3a　　　FIG. 3b　　　FIG. 3c
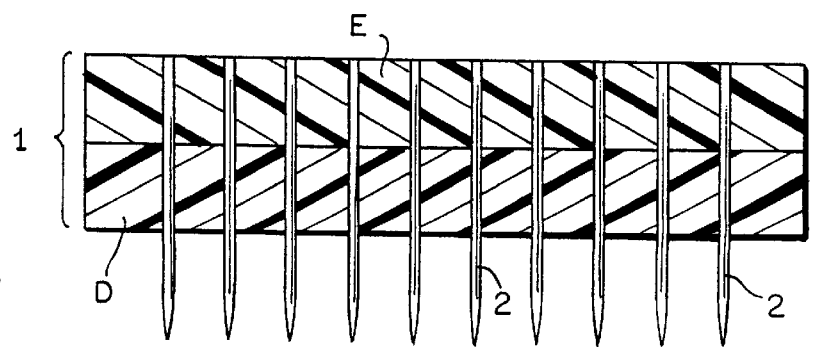
FIG. 4

METHOD OF REPAIRING PERFORATED SUBMUCOSAL TISSUE GRAFT CONSTRUCTS

This is a divisional of application Ser. No. 08/628,789 filed Apr. 5, 1996. now U.S. Pat. No. 5,755,791.

FIELD OF THE INVENTION

This invention relates to tissue graft constructs useful in promoting regrowth and healing of damaged or diseased tissue structures. More particularly this invention is directed to perforated submucosal tissue graft constructs formed from submucosal tissue of a warm-blooded vertebrate and a method for making said constructs.

BACKGROUND AND SUMMARY OF THE INVENTION

It is known that compositions comprising the tunica submucosa delaminated from both the tunica muscularis and at least the luminal portion of the tunica mucosa of the intestine of warm-blooded vertebrates can be used as tissue graft materials. See, for example, U.S. Pat. Nos. 4,902,508 and 5,281,422. The compositions described in those patents are characterized by excellent mechanical properties, including high compliance, a high burst pressure point, and an effective porosity index which allows such compositions to be used beneficially for vascular graft constructs and in connective tissue replacement applications. When used in such applications the submucosal graft constructs appear to serve as a matrix for the regrowth of the tissues replaced by the graft constructs. Significantly, too, in over 600 cross-species implants, submucosa-derived graft compositions have never been shown to elucidate a tissue graft rejection reaction.

Submucosa-derived matrices for use in accordance with the present invention are collagen based biodegradable matrices comprising highly conserved collagens, glycoproteins, proteoglycans, and glycosaminoglycans in their natural configuration and natural concentration. One extracellular collagenous matrix for use in this invention is submucosal tissue of a warm-blooded vertebrate. Submucosal tissue can be obtained from various sources, for example, intestinal tissue harvested from animals raised for meat production, including, pigs, cattle and sheep or other warm-blooded vertebrates. Vertebrate submucosal tissue is a plentiful by-product of commercial meat production operations and is thus a low cost tissue graft material.

One limitation of the submucosal graft constructs described in the above mentioned patents is that the size of the graft is restricted by the size of the source material from which the submucosal tissue is prepared. For example, the size of a submucosal tissue graft prepared from intestinal tissues is limited by the length and circumference of the source segments intestinal tissue. Yet several applications of submucosal tissue graft constructs, including hernia repair, skin graft, meningeal coverings, repair of gastroschisis (congenital stomach defects) and organ tissue replacement, often require larger sheets of graft material than can be prepared directly from natural sources.

Large sheets of submucosal tissue can be prepared from smaller segments of submucosal tissue through conventional techniques such as weaving, knitting or the use of adhesives. However, commercial implementation of such techniques are often impractical and expensive. Additionally the use of adhesives or chemical pretreatment to promote adhesion of the tissue strips can compromise the biotropic properties of the submucosal grafts. Thus there is a need for an inexpensive, easily manufactured, large area submucosal tissue graft construct that retains its biotropic properties.

In accordance with one embodiment of the present application large area submucosal tissue graft constructs are formed from multiple pieces of vertebrate submucosa-derived matrices. Unitary sheets (i.e. single piece graft constructs) of submucosal tissue are prepared in accordance with the present invention by fusing multiple strips of submucosal tissue to each other to form a sheet of tissue having a surface area larger than any one of the component strips of submucosal tissue. The process comprises the steps of overlapping at least a portion of one strip of submucosal tissue with at least a portion of another strip of submucosal tissue and applying pressure at least to said overlapped portions under conditions allowing dehydration of the submucosal tissue. Under these conditions the overlapped portions will become "fused" to form a unitary large sheet of tissue. These large area graft constructs consist essentially of submucosal tissue, free of potentially compromising adhesives and chemical pretreatments, and have a greater surface area and greater mechanical strength than the individual strips used to form the graft construct.

Individual strips of submucosal tissue as prepared from the tissues of a warm-blooded vertebrate have mechanical properties that are directionally specific (i.e. physical properties vary along different axes of the tissue). These directional characteristics are governed primarily by collagen orientation within the tissue. The collagen fibers are the load bearing constituents within intestinal submucosal tissue and are predominantly orientated parallel to the axis of the intestine lumen. This longitudinal disbursement of collagen in intestinal submucosal tissue contributes to the directional variability in physical properties of the submucosal tissue constructs.

Unitary pseudoisotropic multi-laminate graft constructs can be prepared from multiple strips of submucosal tissue. The term "pseudoisotropic" as used herein describes a graft material having approximately similar physical properties along each axis of the graft material. These pseudoisotropic multi-laminate graft constructs are prepared from individual strips of submucosal tissue or sheets of submucosal tissue comprising strips of submucosal tissue. The method of preparing the pseudoisotropic graft constructs comprises overlapping a portion of a first strip (or sheet) with a second strip (or sheet), wherein the second strip (or sheet) is orientated in a plane parallel to the first strip (or sheet) but rotated so that the longitudinal axis of the first strip (or sheet) forms an angle relative to longitudinal axis of the second strip (or sheet). Additional strips (or sheets) can be added in a similar manner to create a multi-laminate structure having a desired number of laminate layers. The individual submucosal strips (or sheets) are then fused to one another to form a unitary multi-laminate pseudoisotropic construct by applying pressure at least to the overlapped portions of submucosal tissue.

SUMMARY OF THE INVENTION

The present invention is directed to an improved submucosal tissue graft construct. The improvement comprises forming a plurality of perforations in the submucosal tissue graft constructs. The perforations allow extracellular fluids to pass through the tissue graft material, decreasing fluid retention within the graft and enhancing the remodeling properties of the tissue grafts. The perforation of the submucosal tissue is especially beneficial for multi-laminate tissue graft constructs wherein the perforations also enhance the adhesive force between adjacent layers.

BRIEF DESCRIPTION OF THE DRAWINGS

FIGS. 1a–1c are diagrammatic representations of the steps of preparing a homolaminate graft construct from multiple strips of submucosal tissue.

FIGS. 2a–2c are diagrammatic representations of the steps of preparing a pseudoisotropic heterolaminate graft construct formed from four strips of submucosal tissue.

FIGS. 3a–3c are diagrammatic representations of the steps of preparing a pseudoisotropic heterolaminate graft construct from three sheets of submucosal tissue, wherein each sheet is formed from multiple strips of submucosal tissue.

FIG. 4 is a diagrammatic representation of one device suitable for forming perforations in submucosal tissue grafts in accordance with the present invention.

DETAILED DESCRIPTION OF THE PREFERRED EMBODIMENTS

There is provided in accordance with this invention an improved submucosal tissue graft construct, the improved construct comprising a submucosal tissue graft having a plurality of perforations extending through the graft. In preferred embodiments the perforations are uniform in size and are evenly distributed over the entire surface of the graft. Furthermore, the present invention provides a method for preparing perforated submucosal tissue graft constructs.

Submucosal tissue suitable for use in the formation of the present graft constructs comprises naturally associated extracellular matrix proteins, glycoproteins and other factors. One source of submucosal tissue is the intestinal tissue of a warm-blooded vertebrate. Small intestinal tissue is a preferred source of submucosal tissue for use in this invention.

Suitable intestinal submucosal tissue typically comprises the tunica submucosa delaminated from both the tunica muscularis and at least the luminal portion of the tunica mucosa. In one embodiment of the present invention the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and optionally sterilized.

The multi-laminate submucosal tissue graft constructs of the present invention can be sterilized using conventional sterilization techniques including glutaraldehyde tanning, formaldehyde tanning at acidic pH, propylene oxide or ethylene oxide treatment, gas plasma sterilization, gamma radiation, electron beam, peracetic acid sterilization. Sterilization techniques which do not adversely affect the mechanical strength, structure, and biotropic properties of the submucosal tissue is preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation), ethylene oxide treatment or gas plasma sterilization; peracetic acid sterilization is the most preferred sterilization method. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

Submucosal tissue can be stored in a hydrated or dehydrated state. Lyophilized or air dried submucosa tissue can be rehydrated and used in accordance with this invention without significant loss of its biotropic and mechanical properties.

Large area compliant sheets of submucosal tissue can be formed from multiple strips of submucosal tissue. The dimensions of the individual strips of submucosal tissue used is not critical and the term "strip of submucosal tissue" is defined herein to include submucosal tissue from one or more vertebrate sources or organs in a wide variety of sizes and shapes. In one embodiment the strips are formed from a delaminated segment of intestinal tissue that is optionally, but preferably, cut and flattened out to provide an elongated strips of submucosal tissue having two generally parallel sides and opposite ends. The term "sheet of submucosal tissue" is defined herein to include tissue constructs comprising multiple strips of submucosal tissue, wherein the strips are overlapped to form a construct having a greater surface area than any one of the individual sheets used to form said construct. The term "layers of submucosal tissue" refers to the individual laminae of a multi-laminate submucosal tissue construct.

Unitary, large area sheets of submucosal tissue are formed by overlapping individual strips of submucosal tissue and applying pressure to the overlapped portions to fuse the tissues together. In one embodiment pressure is applied to the overlapped tissue under conditions allowing dehydration of the submucosal tissue. The large area sheets of submucosal tissue can be formed as either a heterolaminar sheet or a homolaminar sheet. The term "heterolaminar" as used herein refers to a multi-laminate tissue having a variable number of laminae of submucosa superimposed at (and fused) at different points on the unitary graft construct. The term "homolaminar" as used herein refers to a multi-laminate tissue graft construct having a uniform number of laminae of submucosa at all points on the unitary graft construct.

In one embodiment the method of forming large sheets of submucosal tissue comprises the steps of overlapping at least a portion of one strip of submucosal tissue with at least a portion of a second strip of submucosal tissue, and applying pressure at least to said overlapped portions under conditions allowing dehydration of the submucosal tissue. The amount of tissue overlap between the adjacent strips of submucosal tissue can be varied based on the intended use and the desired properties of the large area graft construct, provided that at least a portion of each strip of submucosal tissue overlaps with a portion of another strip of submucosal tissue. The applied pressure fuses the strips of submucosal tissue to one another along the overlapped portions, producing a compliant unitary heterolaminar sheet of submucosal tissue.

In another embodiment, a unitary homolaminate sheet of submucosal tissue can be prepared from strips of submucosal tissue. The method for forming the homolaminar tissue graft construct comprises the steps of forming a first layer of submucosal tissue, wherein strips of submucosal tissue are located side-by-side on a first surface. The strips of submucosal tissue of the first layer are located adjacent to one another so that the edges of the individual strips are in contact with one another without substantial overlap between one another. The first layer of submucosal tissue is then overlaid with a second layer of submucosal tissue. The strips of submucosal tissue of the second layer are located adjacent to one another similar to the strips of submucosal tissue of the first layer (i.e. adjacent to one another so that the edges of the individual strips are in contact with one another without substantial overlap between one another). In one embodiment the strips of submucosal tissue of the second layer are orientated in the same direction as the strips of submucosal tissue of the first layer, but offset in relationship to the submucosal strips of the first layer, so that the contacting edges of the individual strips of submucosal tissue of the first layer are bridged by the strips of submucosal tissue of the second layer (See FIGS. 1a–1c). The overlap portions of the strips of submucosal tissue are then compressed between two surfaces, at least one of the two surfaces being water permeable, under conditions allowing at least partial dehydration of the compressed submucosal tissue.

Advantageously both the heterolaminar and homolaminar large area sheets of submucosal tissue consist essentially of submucosal tissue, have enhanced mechanical strength and have a greater surface area than any one of the individual strips used to form the submucosal sheets.

Submucosal tissue typically has an abluminal and a luminal surface. The luminal surface is the submucosal surface facing the lumen of the organ source and typically adjacent to an inner mucosa layer in vivo whereas the abluminal surface is the submucosal surface facing away from the lumen of the organ source and typically in contact with smooth muscle tissue in vivo. The multiple strips of submucosal tissue can be overlapped with the abluminal surface contacting the luminal surface, the luminal surface contacting the luminal surface or with the abluminal surface contacting the abluminal surface of an adjacent strip of submucosal tissue. All of these combinations of overlapping strips of submucosal tissue from the same or different vertebrate or organ sources will produce a large area sheet of submucosal tissue upon compression of at least the overlapped portions under conditions allowing dehydration of the tissue.

Strips of submucosal tissue can be conditioned, as described in U.S. Pat. No. 5,275,826 (the disclosure of which is expressly incorporated herein by reference) to alter the viscoelastic properties of the submucosal tissue. In accordance with one embodiment submucosa delaminated from the tunica muscularis and luminal portion of the tunica mucosa is conditioned to have a strain of no more than 20%. The submucosal tissue is conditioned by stretching, chemically treating, enzymatically treating or exposing the tissue to other environmental factors. In one embodiment the strips of intestinal submucosa tissue are conditioned by stretching in a longitudinal or lateral direction so that the strips of intestinal submucosa tissue have a strain of no more than 20%. The conditioned submucosal strips can be used to form large area sheets or multi-laminate structures in accordance with the present invention. Alternatively, the submucosal material can be conditioned after the formation of a large area sheets or multi-laminate large area sheet constructs to produce submucosal tissue material having a strain of no more than 20%.

During formation of the large area sheets of submucosal tissue, pressure is applied to the overlapped portions by compressing the submucosal tissue between two surfaces. The two surfaces can be formed from a variety of materials and in any shape depending on the desired form and specification of the unitary graft construct. Typically the two surfaces are formed as flat plates but they can also include other shapes such as screens, opposed cylinders or rollers and complementary nonplanar surfaces. Each of these surfaces can optionally be heated or perforated. In preferred embodiments at least one of the two surfaces is water permeable. The term water permeable surface as used herein includes surfaces that are water absorbent, microporous or macroporous. Macroporous materials include perforated plates or meshes made of plastic, metal, ceramics or wood.

The submucosal tissue is compressed in accordance with one embodiment by placing the overlapped portions of the strips of submucosal tissue on a first surface and placing a second surface on top of the exposed submucosal surface. A force is then applied to bias the two surfaces towards one another, compressing the submucosal tissue between the two surfaces. The biasing force can be generated by any number of methods known to those skilled in the art including the passage of the apparatus through a pair of pinch rollers (the distance between the surface of the two rollers being less than the original distance between the two plates), the application of a weight on the top plate, and the use of a hydraulic press or the application of atmospheric pressure on the two surfaces.

In one preferred embodiment the strips of submucosal tissue are subjected to conditions allowing dehydrating of the submucosal tissue concurrent with the compression of the tissue. The term "conditions allowing dehydration of the submucosal tissue" is defined to include any mechanical or environmental condition which promotes or induces the removal of water from the submucosal tissue at least at the points of overlap. To promote dehydration of the compressed submucosal tissue, at least one of the two surfaces compressing the tissue is water permeable. Dehydration of the tissue can optionally be further enhanced by applying blotting material, heating the tissue or blowing air across the exterior of the two compressing surfaces.

The multiple strips of submucosal tissue are typically compressed for 12–48 hours at room temperature, although heat may also be applied. For example a warming blanket can be applied to the exterior of the compressing surfaces to raise the temperature of the compressed tissue up to about 40° C. to about 50° C. The overlapped portions are usually compressed for a length of time determined by the degree of dehydration of the tissue. The use of heat increases the rate of dehydration and thus decreases the amount of time the overlapped portions of tissue are required to be compressed. Typically the tissue is compressed for a sufficient time to produce a stiff but flexible material. Sufficient dehydration of the tissue is also indicated by a increase in impedance of electrical current flowing through the tissue. When impedance has increased by 100–200 ohms, the tissue is sufficiently dehydrated and the pressure can be released.

The compressed submucosal tissue can be removed from the two surfaces as a unitary compliant large area tissue construct. The construct can be further manipulated (i.e. cut, folded, sutured, etc.) to suit various medical applications where the submucosal material of the present invention is required.

A vacuum can optionally be applied to submucosal tissue during the compression procedure. The applied vacuum enhances the dehydration of the tissue and may assist the compression of the tissue. Alternatively the application of a vacuum may provide the sole compressing force for compressing the overlapped portions of the multiple strips of submucosal tissue. For example the overlapped submucosal tissue is laid out between two surfaces, preferable one of which is water permeable. The apparatus is covered with blotting material, to soak up water, and a breather blanket to allow air flow. The apparatus is then placed in a vacuum chamber and a vacuum is applied, generally ranging from 14–70 inches of Hg (7–35 psi). Preferably a vacuum is applied at approximately 51 inches of Hg (25 psi). Optionally a heating blanket can be placed on top of the chamber to heat the submucosal tissue during the compression of the tissue. Chambers suitable for use in this embodiment are known to those skilled in the art and include any device that is equipped with a vacuum port. The resulting drop in atmospheric pressure coacts with the two surfaces to compress the submucosal tissue and simultaneously dehydrate the submucosal tissue.

Optionally, large area tissue grafts can be formed into various shapes for tissue graft applications. For example, in organ reconstruction applications the large area sheets can be formed in the shape of a hollow sphere or pouch. Such a shaped construct would be advantageous in the replacement of large regions of the urinary bladder or stomach. These shaped submucosal tissue constructs can be formed by conventional techniques such as cutting and suturing the tissue to form a desired shape.

Alternatively, strips of submucosal tissue can be formed into a large sheet of submucosal tissue having a nonplanar shape through a simple manufacturing procedure. The method comprises the steps of placing multiple strips of submucosal tissue between two complementary nonplanar shaped surfaces and compressing overlapped strips of submucosal tissue between the two surfaces. The complementary shaped surfaces are formed such that the two surfaces can be pressed together such that the surfaces fit snug against one another without leaving any substantial pockets of air between the two surfaces. Preferably at least one of the two complementary surfaces is water permeable.

One method of forming a shaped submucosal construct comprises placing multiple strips of submucosal tissue on a nonplanar shaped porous surface such that the submucosal tissue conforms to the shape of the porous surface. Preferably the submucosal tissue is placed on the porous surface without stretching the material, however, the submucosal tissue can be stretched to facilitate covering the shaped porous surface. Each of the strips of submucosal tissue is positioned on the porous surface to overlap at least a portion of an adjacent strip of submucosal tissue. The overlapped portions of the submucosal tissue are then covered with a second shaped surface that is complementary in shape with the first porous surface and pressure is applied to compress the submucosal tissue between the two surfaces under conditions allowing dehydration of the submucosal tissue.

Alternatively the large area sheets of the present invention can be shaped into a nonplanar shape by stretching the large area sheet through the use of a die press procedure, wherein the submucosal tissue is pressed into a nonplanar shape by a porous die under dehydrating conditions such that the formed tissue graft holds its shape. Preferably a multi-laminate large area sheet is used in such a procedure.

Multi-laminar submucosal tissue constructs are formed in accordance with the present invention by overlapping a portion of one strip of submucosal tissue with a portion of another strip of submucosal tissue. In a similar fashion large area multi-laminar tissue graft constructs can be formed in accordance with the present invention by overlapping a sheet of submucosal tissue (formed as described above) with at least a portion of a second sheet of submucosal tissue. The size and physical properties of the multi-laminate submucosal tissue construct can be regulated by the number of overlapped strips of submucosal tissue and the percent of the overlapped portion of each strip.

The multi-laminar tissue graft constructs are formed in accordance with the present invention by overlapping at least a portion of one strip of submucosal tissue with a portion of another strip of submucosal tissue to form a first sheet. Additional strips of submucosal tissue are overlaid onto the overlapped portions of the first sheet to form a second sheet, wherein the edges of the strips of the second sheet are optionally at an acute angle to the edges of the strips in the first sheet, and wherein said formed second sheet is coplanar with the first sheet. The strips of submucosal tissue of the second sheet can be positioned so that at least a portion of one strip of submucosal tissue of the second sheet overlaps with at least a portion of another strip of submucosal tissue of the second sheet. Additional strips of submucosal tissue can be overlaid on the overlapped portions of the first and second sheets to provide additional layers of submucosal tissue. The multiple layers of submucosal tissue are then compressed under dehydrating conditions to form a multi-ply heterolaminar submucosal tissue construct having a surface area greater than any one of the individual strips of submucosal tissue used to form the multilayered construct.

In one embodiment of the present invention submucosal tissue is cut to into strips, each strip having generally parallel sides, and used to form the multilayered heterolaminar construct of the present invention. In this embodiment the strips of submucosal tissue of the second sheet are overlaid onto the overlapped portions of the first sheet such that the edges of the first sheet submucosal strips are at an angle relative to the edges of the second sheet submucosal strips. The overlapped portions of submucosal tissue are compressed under dehydrating conditions to form the multilayered heterolaminar construct.

The multi-laminate tissue graft constructs can be formed to have pseudoisotropic properties. These pseudoisotropic tissue grafts are prepared from at least three strips of intestinal submucosal tissue delaminated from both the tunica muscularis and the luminal portion of the tunica mucosa of a warm blooded vertebrate. Each of the strips of intestinal submucosal tissue are characterized as having a longitudinal axis corresponding to the predominant orientation of the collagen fibers in the submucosal tissue strips. The method of forming the pseudoisotropic graft constructs comprises locating a first strip of submucosal tissue on a first surface, overlaying said first strip with at least two additional strips of submucosal tissue so that the longitudinal axes of each individual strip of submucosal tissue forms an angle of about 180°/N with the longitudinal axis of at least two other strips of submucosal tissue forming the heterolaminate graft, wherein N=the total number of strips of submucosal tissue. (See FIGS. 2a–2c). For example a pseudoisotropic graft construct formed from four (4) strips of submucosal tissue will have an angle of 45° (180°/4=45°) formed between the central longitudinal axes of each strip in reference to two of the other three strips forming the graft construct. (See FIGS. 2a–2c). The submucosal tissue (at least the overlapped portions) is then compressed between the first surface and a second surface. In one embodiment the tissue is compressed under conditions allowing at least partial dehydration of the compressed submucosal tissue, and in a preferred embodiment at least one of said surfaces is water permeable. Advantageously the submucosal tissue grafts are fused together in accordance with the present invention in the absence of adhesives or sutures.

Large area tissue graft constructs having pseudoisotropic properties can also be prepared from large area sheets of submucosal tissue. These pseudoisotropic tissue graft constructs comprise multiple layers of large area sheets of submucosal tissue wherein the sheets of submucosal tissue comprise overlapped strips of submucosal tissue. As described above, large area sheets of submucosal tissue can be formed from overlapped submucosal tissue to form either heterolaminar or homolaminar sheets of submucosal tissue. Both heterolaminar and homolaminar sheets are suitable for forming large area pseudoisotropic tissue graft constructs in accordance with the present invention (See FIGS. 3a–3c).

One method of preparing a large area multi-laminate tissue graft construct having pseudoisotropic properties comprises forming a first sheet of submucosal tissue from multiple strips of submucosal tissue and overlaying the first sheet with at least two additional sheets. The individual strips of submucosal tissue comprising each sheet have a longitudinal axis corresponding to the predominant orientation of the collagen fibers in the submucosal tissue strips. The first sheet is formed on a first surface by overlapping the individual strips of submucosal tissue so that each strip is aligned with the adjacent strips and the longitudinal axis of each strip of submucosal tissue are substantially parallel to one another. Thus the collagen fibers of the first sheet are aligned predominantly in a single orientation, such that the sheet can be characterized as having a longitudinal axis corresponding to the predominant orientation of the collagen fibers. The sheet has a greater surface are than any one of the individual strips used to form the sheet.

After the first sheet of submucosal tissue is formed, additional submucosal sheets are formed on top of the first sheet in the same manner that the first sheet was formed (i.e. each sheet of submucosal tissue of the multi-laminate comprises overlapped strips of submucosal tissue wherein the longitudinal axes of the strips of submucosal tissue comprising each sheet are substantially parallel to one another). Each individual sheet is overlaid on another sheet so that the longitudinal axes of the strips of submucosal tissue of the overlaid sheet forms an angle of about 180°/S (S=the total number of sheets of submucosal tissue), with the longitudinal axes of the strips of submucosal tissue of at least two of the other sheets forming the multi-laminate construct. Once the total number of sheets have been overlaid, the sheets of submucosal tissue are compressed between the first surface and a second surface under conditions allowing at least partial dehydration of the compressed submucosal tissue. In preferred embodiments at least one of said surfaces is water permeable.

In one embodiment, after multiple strips of submucosal tissue are overlapped with one another, the overlapped portions are manipulated to remove trapped air and bulk quantities of water before fusing the strips into a single sheet of submucosal tissue. In general the trapped air bubbles and bulk quantities of water are squeezed out through the use of a compressing force which is moved across the surface of the overlapped portions. The compressing force can take the form of a cylinder that is rolled across the surface of the overlapped portions, or alternatively the overlapped portions can be passed between two or more rollers wherein the distance between the surface of the opposing rollers is less than the thickness of the submucosal sheet. The overlapped portions can then be compressed if necessary for an additional length of time under dehydrating conditions to fuse the multiple strips into a single sheet of submucosal tissue in accordance with the present invention.

The excess portions of the pseudoisotropic multi-laminate grafts (i.e. those portions of the graft having a laminate number less than N or S) can be removed after formation of the multi-laminate. Furthermore, the mechanical properties of multi-laminate submucosal material can be tailored to the medical application needs by adjusting the percentage of overlap between adjacent strips of submucosal tissue, altering the number of submucosal tissue layers, varying the angle of adjacent layers relative to one another, changing the water permeability of the compressing surfaces and/or the composition of the compressing surfaces, selecting the shape of the compressive surfaces, and varying the load applied to compress the overlapped submucosal tissue.

The present invention is directed to a modification that improves the efficacy of large area and multi-laminate submucosal graft constructs as implantable graft materials. Recent experiments have demonstrated that the process of remodelling is slower with implanted multi-laminate submucosal tissue graft constructs than for single or two layered submucosal tissue grafts. In addition, multi-laminate submucosal tissue graft constructs tend to accumulate tissue fluid in cyst-like pockets between adjacent laminae during the first 14–28 days after implantation in soft tissue locations (such as the muscular body wall of rats). Fluid pockets are detrimental to wound healing because they retard connective tissue ingrowth, provide an environment conducive to bacterial growth, and prevent the apposition of natural (native) body tissues which promotes healing and tensile strength.

The present invention minimizes the disadvantages associated with multi-laminate submucosal tissue graft constructs by forming perforations in the graft constructs. Perforation of the graft constructs has been found to enhance the graft's in vivo remodelling properties and to enhance the adhesion of the tissue graft layers to one another. The perforations are believed to promote contact of the submucosal tissue with endogenous fluids and cells (by increasing the surface area of the implanted graft) and the perforations also serve as a conduit allowing extracellular fluid to pass through the graft.

In accordance with the present invention the term "perforate" designates a bore that extends through the entire graft construct. However, tissue graft constructs having "holes", defined herein as a cavity that penetrates into the tissue but does not extend through the entire graft construct, are also within the scope of the present invention. The spacing and size of the perforations, as well as the depth to which the perforations penetrate into the tissue, will be varied according to the desired mechanical strength, porosity, size and thickness (number of layers) and other factors related to the medical application of the tissue graft. The size of the perforations range from 0.5 to 3 mm, more preferably from 0.6 to 2 mm. The perforations are spaced from one another at a distance ranging from 2 to 20 mm, more preferably from 3 to 7 mm, and in one embodiment the perforations are uniformly spaced from one another. Note that if the perforations are uniformly spaced from one another at a distance of 0.7 cm, then there are 1.43 perforations/cm and 2 perforations/cm$^2$ (1.43×1.43=2.0). Thus in accordance with one embodiment the surfaces of the multi-layered construct are perforated with at least 2 perforations per cm$^2$.

The perforations are formed in the submucosal tissue while the tissue remains at least partially hydrated. In large area sheets or multi-laminate submucosal tissue constructs, comprising multiple strips of submucosal tissue fused together, the perforations are preferably made after formation of the large area sheet/multi-laminate construct and when the tissue is has been dried to a water content of approximately 10–20% by weight water (10–20% hydrated). Sufficient drying of the tissue can be determined by weighing the fresh tissue and drying the tissue to 10–20% of the fresh weight or the sufficient drying can be determined by impedance measurement as previously described. After perforation of the tissue the submucosal tissue is subjected to terminal sterilization and stored as described previously.

In one embodiment holes (extending only part way through the tissue) or perforations can be formed on both sides of the tissue graft. In addition the tissue can be modified to include perforations as well as holes that extend only part way through the tissue. Furthermore the submucosal tissue can be modified to include a plurality of holes, wherein various subsets of holes extend to different depths into the tissue relative to the other formed holes. This can be accomplished, for example, by perforating the individual layers of submucosal tissue before overlapping the layers to form the multi-laminate construct. If some of the layers are not perforated or if the perforations of the individual layers are not aligned, the formed multi-laminate construct will have holes extending to different depths into the tissue. Preferably the tissue is perforated, in a uniform distribution over the surfaces of the tissue graft, thus forming a series of bores that allow fluid communication from a the first planar surface to a second opposite planar surface of the graft construct.

In one embodiment the perforations are formed perpendicular to the surface of the tissue graft construct, i.e., the longitudinal axis of the perforation/hole forms a 90° angle with the plane defining the surface of the graft. Alternatively the perforations can be formed so that the axis of perforation is not perpendicular to the surface of the graft (i.e. so that a longitudinal axis parallel to the wall defining the perforation/hole forms an angle other than 90° with the plane of the graft surface). In accordance with one embodiment the perforations are formed at an angle ranging from 45° to 90° in reference to the surface of the graft.

The perforation of submucosal tissue is anticipated to have its greatest impact on multi-laminate submucosal graft constructs. Multi-laminar tissue grafts can be cut without unraveling and do not delaminate when soaked in water for a period of time (greater than one hour) that corresponds to the time required for implanting the sheet in a host. However, multi-laminate tissue constructs tend to accumulate tissue fluid in cyst-like pockets between adjacent laminae during the first 14–28 days after implantation in soft tissue locations (such as the muscular body wall of rats). Perforations of the multi-laminate graft construct will alleviate the accumulation of fluids between the layers of the multi-laminar construct by providing a conduit through which the fluid can flow out of the tissue. In addition the perforations will have a "stapling" effect that will augment the adhesion of the laminae to each other.

Accordingly, the placement of full thickness or partial thickness holes in multi-laminate tissue grafts provide the following advantages over non-perforated multi-laminate sheets:

1. Increased passage of fluids (including tissue fluids) through the material; and
2. Increased adhesive force between adjacent layers.

The submucosal tissue can be perforated using a wide variety of devices know to those skilled in the art. The method utilized to perforate the submucosal tissue is not critical provided the aggregate structural integrity of the submucosal tissue is maintained.

In preferred embodiments the perforation of the submucosal tissue does not result in the removal of significant amounts of tissue. For example, the perforations are formed by pressing a pointed solid object through the tissue to press the tissue aside during the insertion of a solid object as opposed to boring out the material. Other means for perforating the tissue include the use of ballistics, cutting instruments, laser beams or enzymatic or chemical treatments.

In one embodiment, the submucosal tissue is perforated by pressing a pin or solid needle, into/through the tissue. Typically a 20–23 gauge solid needle is used to form the perforations. In this manner, no significant amount tissue is removed during the process of forming the perforations, but rather a portion of each layer is torn and pushed into an adjacent layer to provide a stapling effect. This "stapling" effect can be further enhanced by forming a portion of the perforations from one side of the graft and forming the remaining perforations from the opposite side of the graft.

FIG. 4 depicts one embodiment of a device for perforating the submucosal tissue graft constructs. The device comprises a base (1) and a plurality of stainless steel pins (2) embedded in base (1) and extending out through the surface of the base. The base comprises Epoxy (E) and Delrin (D) portions and has a length of 3.2 inches, a width of 1.85 inches and is 0.5 inches thick. The Epoxy and Delrin portions each have a length of 3.2 inches, a width of 1.85 inches and are 0.25 inches thick. In accordance with this embodiment pins (2) are substantially parallel to one another and form a 90° angle with the surface of the base. Pins (2) are 0.040 inches in diameter, are spaced 0.264 inches apart (center to center of adjacent pins) within a 0.4 border from the edge of the device and protrude 0.25 in. from the base. The device thus holds a total of fifty pins.

EXAMPLE 1

Submucosal tissue was prepared from vertebrate intestinal tissue in accordance with the procedure described in U.S. Pat. No. 4,902,508. Strips of submucosal tissue were formed from a segment of intestinal tissue of a warm-blooded vertebrate, said segment comprising the tunica submucosa delaminated from both the tunica muscularis and at least the luminal portion of the tunica mucosa of said segment of intestinal tissue. The segment of intestinal tissue was cut along the longitudinal axis of the segment and laid flat. The tissue was then further sliced into a series of strips each having generally parallel sides.

Multiple strips of submucosal tissue were organized on a 12 by 12 inch perforated stainless steel plate wherein a portion of one strip of submucosal tissue overlaps a portion of the adjacent strip of submucosal tissue. A second 12 by 12 inch perforated stainless steel plate was then placed on top of the submucosal tissue. The perforated stainless steel plates used in this embodiment has 0.045 inch perforations arranged straight center and located 0.066 inches apart. A 50–100 pound weight was placed on top of the second stainless steel plate and the tissue was compressed for 24 hours at room temperature.

EXAMPLE 2

Strips of submucosal tissue were prepared as described in Example 1. Multiple strips of submucosal tissue were laid out between two perforated, stainless steel plates so that a portion of one strip of submucosal tissue overlapped a portion of the adjacent strip of submucosal tissue. The "plate-submucosa-plate" apparatus was placed on a flat surface and covered with blotting material, to soak up water, and a breather blanket to allow air flow. The apparatus was then sealed into a nylon bag that has a vacuum port. A vacuum was applied (greater than 28 inches of Hg) to pull air out of the vacuum bag and the resulting drop in atmospheric pressure simultaneously compressed and dehydrated the submucosal tissue. After 24 hours of applying a vacuum, the produced sheet was moist and very flexible. No seams from the layering of the submucosal tissue were visible and the strength of a prototype 8-thickness sheet as determined by ball burst test was 80 pounds.

EXAMPLE 3

Strips of submucosal tissue were prepared as described in Example 1. The submucosal tissue strips were organized on a mesh so that a portion of one strip of submucosal tissue overlapped a portion of the adjacent strip of submucosal tissue. Once the mesh was covered with one layer of submucosal tissue a second layer of submucosal tissue was applied on top of the first layer so that the edges of the submucosal strips of the second layer were at an angle relative to edges of the submucosal strips of the first layer.

After all the strips of submucosal tissue were placed on the mesh, another mesh was placed on top of the submucosal tissue layers and the "mesh-submucosal tissue-mesh" sandwich was compressed with a load and dried. This process produced a dried large area submucosal sheet that was pealed off the mesh as a unitary graft construct.

EXAMPLE 4

Sterilization of Submucosal Tissue with Peracetic Acid

Submucosal tissue is soaked in a peracetic acid/ethanol solution for 2 hours at room temperature using a ratio of 20:1 (mls peracetic solution: grams submucosal tissue) or greater. The peracetic acid/ethanol solution comprises 4% ethanol, 0.1% (volume:volume) peracetic acid and the remainder water. The 0.1% peracetic acid component is a dilution of a 35% peracetic acid stock solution commercially available and defined as in table 1. Preferably, the submucosal tissue is shaken on a rotator while soaking in the peracetic acid solution. After two hours, the peracetic acid solution is poured off and replaced with an equivalent amount of lactated Ringer's solution or phosphate buffered saline (PBS) and soaked (with shaking) for 15 minutes. The submucosal tissue is subjected to four more cycles of washing with lactated Ringer's or PBS and then rinsed with sterile water for an additional 15 minutes.

TABLE 1

Chemical Composition of the 35% Peracetic Acid Solution

| Composition, % by weight | |
|---|---|
| Peracetic acid | 35.5 |
| Hydrogen peroxide | 6.8 |
| Acetic acid | 39.3 |
| Sulfuric acid | 1.0 |
| Water | 17.4 |
| Acetyl peroxide | 0.0 |
| Stabilizer | 500 PPM |

TABLE 1-continued

Chemical Composition of the 35% Peracetic Acid Solution

| Typical active oxygen analysis, % by weight | |
|---|---|
| Active Oxygen as peracid | 7.47 |
| Active Oxygen as $H_2O_2$ | 2.40 |
| Total active oxygen | 10.67 |

Sterilization of Submucosal Tissue with Ethylene Oxide

After preparation of the multi-laminate constructs using sterile conditions, the material is packaged and subjected to a second round of sterilization (terminal sterilization). The tissue can be packaged in plastic that is permeable to ethylene oxide and subjected to ethylene sterilization according to procedures known to those skilled in the art. Essentially the packaged material is exposed to ethylene oxide for four hours at 115° F. During the sterilization the tissue is also provided with 65% relative humidity for at least 75 minutes of the 4 hour treatment. The high humidity enhances uptake of the ethylene oxide by the tissue. After four hours the ethylene oxide, ethylene chlorohydron and ethylene glycol is flushed out with nitrogen and air.

EXAMPLE 5

Ball Burst Strength Test by Means of a Compression Cage and a MTS Tensile Tester The strength of multi-laminate submucosal tissue grafts is determined through the use of a material testing system (MTS) tensile tester. The multi-laminate tissue construct is secured within a four sided frame clamp (specimen clamp) to provide uniform distribution of the stress through out the tissue construct. The initial fixture level is set so that the top of the steel ball is located immediately under the plane the test specimen. The handle of the specimen clamp is lifted to its topmost position so that the jaws of the clamp are able to accept the test specimen. The submucosal tissue construct is cut to fit the specimen clamp, the aperture of the clamp having a diameter of one and three-quarter inches. A half-inch of excess material should be included around the perimeter of the test specimen to ensure sufficient clamping area. The submucosal tissue is placed in jaws of the clamp and secured, the clamp force being controlled by thumbwheel means located on the top clamp.

The clamped submucosal tissue is then pressed down over a metal ball at a controlled rate utilizing a tensile tester software interface to control and measure the force placed on the test specimen. The force is increased until failure of the specimen occurs. Failure is defined as the maximum load which corresponds to the first appearance of the ball through visible non-natural discontinuities in the plane of the specimen. In the case that the topmost position of the fixture is reached prior to failure, the software limits will engage and discontinue the test. The peak load value displayed on the Microprofiler 458.01 is recorded and the specimen is removed.

EXAMPLE 6

A multi-laminate tissue graft construct was prepared as follows:

An ample amount of submucosal tissue is prepared from vertebrate intestine, cut and flattened out and disinfected with peracetic acid as described in Example 4 (approximately 70 grams of submucosal tissue is required for a 10 cm×15 cm device). Surgical gloves, face mask, and cap should be worn after sterilization of the tissue with peracetic acid to minimize the contamination from organic matter and airborne particulate.

Strips of submucosal tissue are placed on top of a first perforated stainless steel plate in the desired orientation. The stainless steel plates used are perforated stainless steel plates with 0.045 inch round perforations on straight centers and located 0.066 inches apart. After formation of a layer of submucosal tissue the submucosal tissue is smoothed out to remove air bubbles. Additional layers are overlaid until the device is complete. Excess material is removed from around the multi-laminate structure with a scissors. The weight of the submucosal multi-laminate is recorded. A second stainless steel plate (perforated with 0.045 inch round perforations on straight centers located 0.066 inches apart) is placed on top of the multi-laminate construct.

The multi-laminate construct can optionally be "pinch rolled" to remove trapped air and water. To pinch roll the material, the two perforated metal plates surrounding the submucosal tissue are placed in-between two polypropylene sheets (Kimberly Clark, class 100 "Crew Wipe") and the entire apparatus is placed in-between two layers of nylon bagging film (Zip Vac, Auburn Wash.) that are larger than 1°×1°. A weighted cylinder is then rolled across the apparatus numerous times (at least three times).

To perforate the multi-laminate submucosal tissue graft construct the apparatus is partially disassembled to expose the top surface of the tissue graft and a piece of nylon bagging film is placed directly on the top most layer of submucosa tissue. The multi-laminate submucosal tissue graft construct is then inverted onto a Styrofoam work surface, and the first stainless steel plate is carefully removed. The exposed surface of submucosa is then covered with a piece of nylon bagging film. The tissue graft construct is then perforated, and then the top nylon bagging film is removed. The multi-laminate submucosal tissue graft construct is then re-inverted and placed back on the perforated stainless steel plate. The nylon bagging film is removed from the submucosa top surface and a second perforated stainless steel plate is placed on top of the multi-laminate submucosal tissue graft construct.

The multi-laminate submucosal tissue graft construct is then compressed under dehydrating conditions as follows:

A layer of blotting material (NuGauze) larger than the size of the perforated plates is placed on a table top (or other smooth level surface). The stainless steel plates with the multi-laminate submucosal tissue graft construct between them is placed on top of the blotting material. Another layer of blotting material (approximately the same size as the first sheet of blotting material) is placed on top of the stainless steel plates. A breather blanket (Zip Vac, Auburn, Wash.) is placed on top of the blotting material. Preferably the breather blanket is slightly larger than the objects it is covering.

Optionally electrodes can be placed in contact with the submucosal tissue to allow the measurement of impedance across the tissue. Typically the tissue is compressed for a sufficient time to produce a stiff but flexible material. Sufficient dehydration of the tissue is indicated by a increase in impedance of electrical current flowing through the tissue. When impedance has increased by 100–200 ohms, the tissue is sufficiently dehydrated and the pressure can be released.

A border of chromate tape is placed on the table top around the apparatus and the area to be vacuum pressed The backing is removed from the tape and a piece of the nylon bagging film that already has the nozzle port attached to it is placed on top of the area enclosed by die chromate tape (see FIGS. 3a & 3b) and adhered to the tape. The heating blanket, if used is turned on, and vacuum pump is turned on. The bag should be checked for wrinkles (smooth them out if found) and for an inadequate seal between the chromate tape and the nylon bagging film (correct if found). A vacuum should be drawn to a level ranging from 25 to 30 $\text{psi}_{vac}$. After vacuuming to the desired hydration level (approximately 24 hours), the seal of the bag is broken at a taped region, the vacuum pump is turned off and the unitary, perforated multi-laminate submucosal tissue graft construct is removed. A pair of scissors can be used to cut off any portion of the tissue graft that did not receive the complete amount of overlap.

EXAMPLE 7

The submucosal tissue graft construct can also be perforated after formation of the unitary multi-laminate construct as follows. The multi-laminate construct is formed in accordance with Example 3. The mesh/submucosal tissue sandwich was removed from the drying apparatus and the tissue was perforated. The graft was perforated by inserting a nail between the mesh of the wire and pushing the nail through the tissue at multiple points on the graft surface. The perforated multi-laminate submucosal tissue was then cut square (4½×4½ in.) and marked for identification purposes.

EXAMPLE 8

A perforated pseudoisolaminate construct was prepared as follows: Strips of submucosal tissue were arranged in 4 layers on a wire mesh. The first layer was laid directly on the mesh and the remaining three layers were overlaid on top of the first layer at an angles of 45° 90° and 135° relative to the first layer, respectively (see FIG. 2). A second mesh was placed on top of the submucosal tissue, and the tissue was sandwiched between the mesh and c-clamped to the drying rack. A fan was placed in front of the rack and turned on. Holes were punched through the tissue in a checkerboard pattern using the mesh as a guide. (i.e. every alternate space in the mesh was used to perforate the tissue. Accordingly the pattern appeared as follows:

```
X       X       X
    X       X
X       X       X
    X       X
```

The perforation of the tissue was stopped before completion because the submucosal tissue was being disrupted. Therefore the submucosal tissue was dried for 25 min. with the fan on high. The remaining perforations were then made in the tissue in accordance with the original pattern.

The sheet was allowed to dry overnight, removed, cut square, and labelled for identification.

EXAMPLE 9

Comparison of the Strength of Perforated and Non-perforated Submucosal Tissue

Eight layered pseudoisotropic multi-laminate tissue graft constructs were prepared in accordance with the present invention. The constructs were perforated (uniformly) and the strength of these constructs was compared to non-perforated constructs using the ball burst test described in Example 5. Three separate experiments were conducted and the force applied at failure was recorded (in pounds).

a) The perforated construct comprised 1.0 mm perforations uniformly spaced at 6.71 mm. Four non-perforated constructs and for perforated constructs were tested and the mean values were determined. The non-perforated construct failed at 94.11±7 pounds whereas the perforated construct failed at 83.572±6 pounds.

b) The perforated construct comprised 1.0 mm perforations uniformly spaced at 6.71 mm. Four non-perforated constructs and four perforated constructs were tested and the mean values were determined. The non-perforated construct failed at 73.71±9 pounds whereas the perforated construct failed at 62.35±2 pounds.

c) Two perforated constructs were compare in this experiment with the non-perforated control: the first perforated construct having 1.0 mm perforations uniformly spaced at 6.71 mm and the second having 1.0 mm perforations uniformly spaced at 3.35 mm. Two non-perforated constructs, two of the first perforated construct and seven of the second perforated construct were tested and the mean values were determined. The non-perforated construct failed at 70.17±12 pounds whereas the first perforated construct failed at 79.94±8 and the second construct at 62.39±7 pounds.

Comparison of Perforated and Non-perforated Submucosal Tissue as Tissue Graft Constructs In the following example multi-laminate tissue graft constructs comprising eight layers were prepared in both perforated and non-perforated form. The perforated constructs were perforated using the device depicted in FIG. 4. The resulting perforated tissue constructs had 0.40" diameter bores regularly spaced intervals (6.7 mm apart).

The study conducted utilized 24 rats. The rats were divided into two groups of 12 each. In the first group, an 8 layered, non-perforated multi-laminate sheet of submucosal tissue was implanted. In the second group, an 8 layered, perforated multi-laminate sheet was implanted. The 12 rats in each group were further subdivided into smaller groups that differed only in the method of terminal sterilization.

1. Subgroup #1 in each major group had no terminal sterilization performed on the final device.
2. Subgroup #2 had 2.5 Mrad gamma irradiation applied to the device as a terminal sterilization method.
3. Subgroup #3 had 1.5 Mrad gamma irradiation applied to the final device as a terminal sterilization method.
4. Subgroup #4 had 1.5 Mrad e-beam irradiation terminal sterilization method to the final device.
5. Subgroup #5 had 1.5 ethylene oxide (conducted at Purdue University) applied to the final device as a terminal sterilization method.
6. Subgroup #6 had 1.5 ethylene oxide (performed at Centurion Labs) applied to the final device as a terminal sterilization method.

Results of these studies (excluding terminal sterilization as a variable) showed that perforation significantly decreased the fluid accumulation between the multi-laminate sheets during the remodeling period. One animal was sacrificed from each subgroup at 14 days and the second animal was sacrificed from each subgroup at 28 days. At 14 days, in the animals receiving the tissue grafts lacking perforations, numerous "cysts" of serosanguinous fluid had accumulated between the multi-laminate sheets and around the graft. In the animals receiving the perforated tissue grafts, the amount of fluid accumulation was significantly less, both in terms of the number of cysts and the size of cysts.

By 28 days, there was virtually no evidence for fluid accumulation in the graft of the group receiving the perforated tissue grafts whereas the group receiving the non-perforated tissue grafts still had small pockets of fluid present.

Accordingly, perforating the submucosal tissue before implantation into the host has a significant effect upon healing and remodeling. Perforations appeared to serve as a conduit through which fluid could flow through the entire graft rather than accumulate between sheets. In addition, there was no visible separation of the layers of the perforated multi-laminate tissue grafts which was at least in part attributed to the perforations.

EXAMPLE 10

Comparison of Submucosal Tissue, Dexon®, and Marlex® as Tissue Graft Constructs for use in Hernia Repair.

The effectiveness of submucosal tissue, Dexon® and Marlex® as tissue graft constructs will be analyzed in two separate animal studies. Study No. I utilizes a dog model and Study No. 2 utilizes a rat model.

Study No.1—Dog Model

Thirty dogs are randomly divided into three groups of ten dogs each. A full-thickness body wall defect is created in the ventral lateral abdominal wall of each dog. The defect measures 5 cm×5 cm (W×L) and leaves the peritoneum intact. The defect will be created lateral to the midline, left side, and involves primarily the abdominal aponeurosis. The lateral portion of the defect reaches the distal portion of the abdominal skeletal muscle layers. The defect site is repaired with one of the three devices: small intestinal submucosa, Dexon®, or Marlex® mesh. Ten animals are utilized in each group (i.e., ten animals are implanted with one of the three devices). Two animals from each group are sacrificed at each of the following times: one week, one month, three months, six months, and two years past implantation. The endpoint of the study is the morphology (both macroscopic and microscopic) of the graft materials and surrounding tissue at the time of sacrifice.

Study No. 2—Rat Model

The experimental design for the rat study is identical to that described above for the dog study with one exception: there are thirty animals in each group and six rats are sacrificed from each group at each timepoint. The endpoint of the study will be the same; that is, the macroscopic and microscopic appearance of the graft material and surrounding tissue at the time of sacrifice.

Specimen Preparation

The hernia repair devices will be prepared as follows:
1. Intestinal submucosal tissue: the submucosal tissue graft constructs for implantation will be prepared as described in Example 3. Raw material will be tested using an axial burst test. Only lots with a mean burst force at 3.0 lbs or greater will be used in fabrication. The configuration parameters for the device include the following:
   a) The strips of submucosal tissue will be overlapped (50% overlap) with adjacent strips to form a two layered large area sheet of submucosal tissue.
   b) A second sheet of submucosal tissue is formed and layered on the first sheet at 45° angle relative to the first sheet of submucosal tissue
   c) A third sheet of submucosal tissue is formed and layered on the first sheet at a 45° angle relative to the second sheet
   d) A forth sheet of submucosal tissue is formed and layered on the first sheet of submucosal tissue relative to the third sheet Thus a homolaminate construct comprising eight layers of intestinal submucosal tissue (delaminated from the tunica muscularis and the luminal portion of the tunica mucosa of a vertebrate species) is prepared. The construct is essentially rectangular in shape having a length width of 10 cm×15 cm. The graft construct is pinch rolled to remove air and water from between the laminate layers and the tissue is perforated using a 20-gauge solid needles. The perforations are evenly spaced at 6–7 mm apart. The construct is compressed under dehydrating conditions and sterilized with ethylene oxide.

2. Dexon®: material use for hernia repair will be obtained through Owens & Minor of Indianapolis.
3. Marlex®: material use for hernia repair will be obtained through Owens & Minor of Indianapolis.

The physical properties of the submucosal tissue grafts will be characterized as follows: Five multi-laminar tissue graft constructs will be prepared as described in this example. The graft constructs will first be tested for sterility and pyrogens, respectively by NAmSA (Northwood, Ohio). One graft construct from the batch of devices will be ball burst tested as described in Example 7. One construct will be stored as a reserve sample for archival. Three of the graft constructs will be implemented. Each graft construct will be identified by manufacturing date and graft construct number. For Dexon® and Marlex®, the devices will be characterized by lot number and manufacturing date as given on the device label.

The dogs used in this study will be purchased from LBL Kennels and the rats used in this study will be purchased from Harlan Sprague Dawley, Inc.

Surgical Procedure

Dogs: Each animal weighs between 18 and 25 kg. Each animal will be anesthetized with intravenous thiopental sodium, intubated, and maintained on inhalation anesthesia with isoflurane and oxygen. Under a surgical plane anesthesia, the surgical site will be clipped and scrubbed. The surgical site will be located at least 3 cm lateral (left) to the midline, and will be in a caudal position such that the site includes only distal fibers of the rectus abdominous muscle.

A longitudinal skin incision will be made with dissection of the subcutaneous tissue being performed to expose an area which measures 5 cm×5 cm in dimensions. A full-thickness defect will be created in the abdominal wall removing all tissues except the skin, subcutis, and peritoneum. The peritoneum and overlying transversalis fascia will be left intact.

The defect site will be repaired with either the submucosal tissue construct, the Dexon® hernia repair device, or the Marlex® mesh hernia repair device. The defect site will be filled with a section of either of these devices that is equal in size to the defect. The devices will be sutured to the adjacent normal body wall tissues with 2-0 prolene suture material. The overlying subcutaneous tissue will be closed following placement of a penrose drain which will exit the skin adjacent to the suture line.

Rats: Each animal will be anesthetized with an intraperitoneal injection of pentobarbital sodium (40 mg/kg) followed by inhalation (nose cone) of methoxyflurane and oxygen as needed to maintain a surgical plane of anesthesia. The surgical procedure will be identical to that described above for the dog with the following exception: the defect site will measure 1.5 cm×1.5 cm in dimensions. The location of the defect will be in the same relative location as described for the dog study; on the ventral lateral abdominal wall. The suture used to secure the repair devices in place will be 2-0 prolene.

We claim:

1. In a method of preparing an improved unitary multilaminate tissue graft construct, said method comprising overlapping at least a portion of a strip of intestinal submucosa tissue with another strip of submucosa tissue, wherein the strips of submucosa tissue are delaminated from both the tunica muscularis and the luminal portion of the tunica mucosa of a warm blooded vertebrate; and comprising at least the overlapped portions of the strips of submucosa tissue under conditions allowing at least partial dehydration of the compressed submucosa tissue;

the improvement comprising the step of perforating the overlapped portions of submucosa tissue to form perforations to decrease fluid retention in the graft and enhance the adhesion of adjacent layers.

2. The method of claim 1, wherein the perforations are uniformly distributed on the surfaces of the graft construct.

3. The method of claim 1, wherein the perforations in the submucosa tissue are prepared by pressing pins into the submucosa tissue.

4. The method of claim 3, wherein the pins are pressed into the submucosa tissue at an angle other than 90° to the plane of the surface of the graft construct.

5. The method of claim 1, wherein the submucosa tissue has been dried to a water content of about 10%–20% by weight at the time the tissue is perforated.

6. The method of claim 1, wherein the strips of submucosa tissue forming said graft construct are orientated so that the graft construct has pseudoisotropic properties.

7. The method of claim 1, wherein the strips of submucosa are conditioned to have a strain of no more than 20%.

8. The method of claim 3, wherein the pins are pressed into the graft construct from two opposite sides of the multi-laminate tissue graft construct.

9. In a method of preparing an improved unitary multi-laminate tissue graft construct, said method comprising overlapping a portion of a strip of intestinal submucosa tissue with another strip of submucosa tissue, wherein each strip of submucosa tissue has first and second planar surfaces and each strip of submucosa tissue is delaminated from both the tunica muscularis and at least the luminal portion of the tunica mucosa of a warm blooded vertebrate, to form a graft construct having a planar surface with a surface area greater than the surface area of any one planar surface of the individual strips of submucosa tissue used to form said construct; and compressing the overlapped portions of the strips of submucosa tissue under conditions allowing at least partial dehydration of the compressed submucosa tissue to form perforations;

the improvement comprising perforating the submucosa tissue to decrease fluid retention in the graft and enhance the adhesion of adjacent layers.

10. The method of claim 9, wherein the submucosa tissue has been dried to a water content of about 10%–20% by weight at the time the graft construct is perforated.

11. The method of claim 9, wherein the perforations are formed by pressing pins into the graft construct from two opposite sides of the multi-laminate tissue graft construct.

12. The method of claim 9, wherein the strips of submucosa tissue forming said graft construct are orientated so that the graft construct has pseudoisotropic properties.

13. In a method of preparing an improved unitary multi-laminate tissue graft construct, said method comprising overlapping at least a portion of a strip of intestinal submucosa tissue with another strip of submucosa tissue, wherein the strips of submucosa tissue are delaminated from both the tunica muscularis and at least the luminal portion of the tunica mucosa of a warm blooded vertebrate; and compressing at least the overlapped portions of the strips of submucosa tissue under conditions allowing at least partial dehydration of the compressed submucosa tissue;

the improvement comprising perforating the overlapped portions of submucosa tissue wherein the perforated portion of the graft has at least 2 perforations per $cm^2$ to decrease fluid retention in the graft and enhance the adhesion of adjacent layers.

14. The method of claim 13, wherein the submucosa tissue has been dried to a water content of about 10%–20% by weight at the time the graft construct is perforated.

15. The method of claim 13, wherein the perforations are formed by pressing pins into the graft construct from two opposite sides of the multi-laminate tissue graft construct.

16. The method of claim 13, wherein the strips of submucosa tissue forming said graft construct are orientated so that the graft construct has pseudoisotropic properties.

17. The method of claim 13, wherein the perforations are formed by pressing pins into the graft construct at an angle other than 90° to the plane of a surface of the graft construct.

18. The method of claim 13, wherein the perforations are uniformly distributed on the graft construct.

* * * * *